Figure 1:
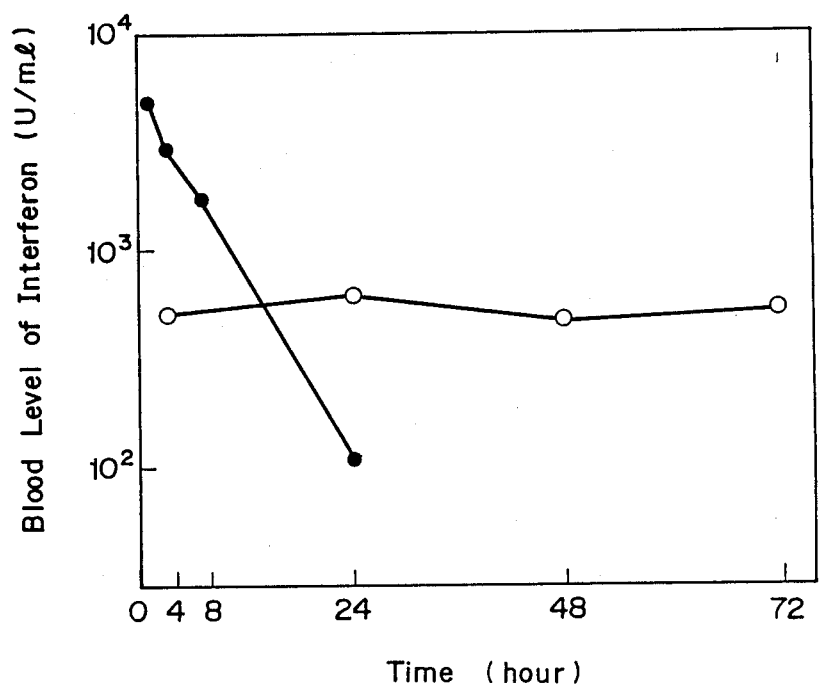

United States Patent [19]

Fujioka et al.

[11] Patent Number: 4,849,141
[45] Date of Patent: Jul. 18, 1989

[54] METHOD FOR PRODUCING SUSTAINED RELEASE FORMULATION

[75] Inventors: Keiji Fujioka, Amagasaki; Shigeji Sato; Yoshio Sasaki, both of Ibaraki; Teruo Miyata, Tokyo; Masayasu Furuse, Sagamihara; Hiromi Naito, Tokyo, all of Japan

[73] Assignees: Sumitomo Pharmaceuticals Company, Limited, Osaka; Koken Co., Ltd., Tokyo, both of Japan

[21] Appl. No.: 946,075

[22] Filed: Dec. 24, 1986

[30] Foreign Application Priority Data

Dec. 27, 1985 [JP] Japan ................ 60-294596
Dec. 27, 1985 [JP] Japan ................ 60-294597
Dec. 5, 1986 [JP] Japan ................ 61-291298

[51] Int. Cl.⁴ .............. B29C 35/00; B29C 47/00; C07G 7/00
[52] U.S. Cl. ........................ 264/207; 264/28; 264/211.11; 264/211.19; 264/232; 264/233; 264/299; 264/330; 424/426; 424/456; 424/457; 514/773; 514/774; 514/801
[58] Field of Search ........... 264/28, 204, 207, 211.11, 264/211.16, 211.13, 299, 330, 211.19, 233; 514/773, 774, 801; 424/426, 456, 457

[56] References Cited

U.S. PATENT DOCUMENTS

| 2,518,510 | 8/1947 | Welch ................ 514/37 |
| 3,016,895 | 1/1962 | Sein . |
| 3,143,475 | 8/1964 | Koff et al. .............. 264/28 |
| 3,857,932 | 12/1974 | Shepherd et al. . |
| 4,164,559 | 8/1979 | Miyata et al. . |
| 4,181,731 | 1/1980 | Yoshida et al. ........ 514/386 |
| 4,193,813 | 3/1980 | Chvapil ............... 264/28 X |
| 4,245,635 | 1/1981 | Kontos . |
| 4,279,812 | 7/1981 | Cioca ................ 530/356 |
| 4,294,241 | 10/1981 | Miyata . |
| 4,347,234 | 8/1982 | Wahlig et al. ......... 424/426 |
| 4,357,312 | 11/1982 | Hsieh et al. .......... 264/28 X |
| 4,374,121 | 2/1983 | Cioca ............... 514/173 X |
| 4,409,332 | 10/1983 | Jefferies et al. . |
| 4,412,947 | 11/1983 | Cioca ................ 530/356 |
| 4,440,680 | 4/1984 | Cioca ................ 530/356 |
| 4,442,051 | 4/1984 | Rowe et al. ........... 264/4.3 |
| 4,483,807 | 11/1984 | Asano et al. ........... 264/22 |
| 4,536,387 | 8/1985 | Sakamoto et al. ..... 424/426 |
| 4,774,091 | 9/1988 | Yamahira et al. ..... 424/426 |

FOREIGN PATENT DOCUMENTS

| 0094157 | 11/1983 | European Pat. Off. . |
| 0098110 | 1/1984 | European Pat. Off. . |
| 0134289 | 3/1985 | European Pat. Off. . |
| 0138216 | 4/1985 | European Pat. Off. . |
| 0139286 | 5/1985 | European Pat. Off. ....... 424/426 |
| 0140255 | 5/1985 | European Pat. Off. . |
| 0170979 | 2/1986 | European Pat. Off. . |
| 2490647 | 3/1982 | France . |
| 56-122317 | 9/1981 | Japan . |
| 51927 | 11/1983 | Japan . |
| 7684 | 2/1984 | Japan . |
| 19925 | 5/1984 | Japan . |
| 642385 | 8/1950 | United Kingdom . |
| 2042888 | 10/1980 | United Kingdom . |
| 2067072 | 7/1981 | United Kingdom . |
| 2091554 | 1/1982 | United Kingdom . |

*Primary Examiner*—Jan H. Silbaugh
*Assistant Examiner*—Mary Lynn Fertig
*Attorney, Agent, or Firm*—Birch, Stewart, Kolasch & Birch

[57] ABSTRACT

A method for preparing a sustained release formulation utilizing collagen and/or gelatin as a carrier, which comprises the steps:
(i) preparing a uniform and high concentrated mixture with respect to the collagen and/or gelatin by blending an active ingredient, said collagen and/or gelatin, and water or an admixture consisting of water and a hydrophilic organic solvent under one of the conditions selected from:
  (A) the pH of the mixture is kept below 5 and the salt concentration of the mixture is retained below fiber-forming concentration;
  (B) chemically modified collagen and/or gelatin is employed; and
  (C) glucose is added to the mixture;
(ii) molding the resultant mixture; and
(iii) gradually eliminating the solvent from the molded product.

11 Claims, 1 Drawing Sheet

METHOD FOR PRODUCING SUSTAINED RELEASE FORMULATION

The present invention relates to a sustained release formulation. More particularly, it relates to a method for producing a sustained release formulation which comprises collagen and/or gelatin as a carrier and a pharmaceutically active ingredient.

Various sustained release formulations are known which are implanted in lesional region of a human or animal body, thereby allowing direct action of an active ingredient to the lesion and preventing the generation of undesirable side-effects. Among them, sustained release formulations composed of a biodegradable and biocompatible carrier such as collagen or gelatin, particularly, those in the form of a needle-like or bar-like shaped mini-pellet (diameter: 0.5–1.5 mm, length: 5–15 mm) which can be administered by means of a forceps needle for fiberscope or an indwelling needle are recognized as being especially advantageous in clinical use (see European Patent Publication No. 0139286A2).

As will be hereinafter discussed, however, collagen and gelatin have undesirable properties which make it difficult to prepare a satisfactory mini-pellet formulation using these materials. Thus, it is not easy, by the use of collagen or gelatin, to prepare a mini-pellet formulation which contains an active ingredient uniformly dispersed and which has constant size and invariable weight. This difficulty mainly arises from "fiber-forming property" of collagen or gelatin as discussed below.

A molding material for preparing a sustained release formulation must be uniform and have a sufficient viscosity, in other words, a sufficient concentration with respect to the carrier, when subjected to the extrusion molding. However, where the molding material consists of collagen or gelatin as the carrier and a protein preparation, i.e., a protein dissolved or suspended in an aqueous inorganic salt solution, as an active ingredient, it is often observed that the molding material cannot exist in the form of a uniform and homogeneous solution because collagen gelatin tends to form fibers under the influence of pH and a salt concentration of the aqueous inorganic salt solution.

Apart from the above inconvenience, the product obtained after the molding process generally takes a distorted shape during air-drying at room temperature. This is because the molded product cannot be uniformly dried by such air-drying.

Under such circumstances as mentioned above, it has been conventional so far that a mixture of an active ingredient and a diluted collagen or gelatin solution is spray-dried or lyophilized, pulverized, and subjected to the compression molding. Another conventional method is that the aforementioned mixture is first placed in the mold, lyophilized and subjected to the compression molding. The molded product, for instance mini-pellets produced by such conventional method are fragile and have relatively short release time. Therefore, it has been impossible so far to produce a long-term sustained-release formulation using collagen or gelatin.

It has now been found that mini-pellets having constant and invariable size and weight can be obtained by preparing, under a certain condition, a uniform and high concentrated mixture with respect to collagen or gelatin by blending collagen or gelatin with water or an admixture consisting of water and a hydrophilic organic solvent, and molding the concentrated mixture, and then gradually eliminating the solvent from the molded product. This invention is based on the above finding.

Thus, an object of the present invention is to provide a method for preparing a sustained release formulation utilizing collagen and/or gelatin as a carrier, which comprises the steps:

(1) preparing a uniform and high concentrated mixture with respect to the collagen and/or gelatin by blending an active ingredient, said collagen and/or gelatin, and water or an admixture consisting of water and a hydrophilic organic solvent;

(2) molding the resultant mixture; and (3) gradually eliminating the solvent from the molded product.

The term "uniform and high concentrated mixture" herein used in connection with collagen and/or gelatin refers to a uniform aqueous mixture containing 10 to 40%, preferably 20 to 30% by weight of collagen and/or gelatin. Such uniform and high concentrated mixture may be successfully obtained without causing fiber-formation under one of the following conditions.

(1) To keep the pH of the mixture below 5 and to keep the salt concentration of the mixture below fiber-forming concentration. Under this condition, a high concentrated mixture of collagen and/or gelatin will not form a fiber and uniformity of the mixture is retained.

"Fiber-forming concentration" mentioned above is defined as follows:

Powdered atelocollagen (1 g) is swollen by mixing with a small amount of distilled water, and then added with HCl to form a solution. On the other hand, a set of salt solutions having various concentrations are prepared. One of them is added to the above solution and the mixture is thoroughly admixed in a mortar and fiber-formation due to atelocollagen is observed. The upper limit of the final concentration of the salt in said mixture which causes no fiber-formation is defined as fiber-forming concentration. The fiber-forming concentration varies depending upon kinds of salt, a concentration of atelocollagen and pH of the mixture. For instance, that of sodium chloride is 0.17 mole when the concentration of atelocollagen and pH of the mixture are 20 w/w % and 3.0 respectively.

(2) To employ collagen and/or gelatin which has been chemically modified by, for instance, succinylation or methylation. This method is advantageous when control of pH of the mixture is essential for ensuring the stability of an active ingredient.

(3) To add glucose to the mixture. This process is particularly advantageous where the mixture has nearly neutral pH, because the solubility of collagen and/or gelatin is increased by such addition.

Collagen employed in the present invention is a protein which is a major component of connective tissue of animals and has less antigenicity, and hence, has widely been used as a surgical suture in various medical operations. Instead of the collagen itself, there may be employed atelocollagen which has far less antigenicity and which is obtained by removing the telopeptide region from the collagen. As previously stated, succinylated or methylated collagen is also employable.

Gelatin is a heat-denatured collagen and pharmaceutically safe compound. It can be chemically modified in the similar manner as collagen.

According to the present invention, collagen or gelatin, or any of their derivatives is employable alone or in any combination of two or more thereof. For the purpose of the present invention, the term "collagen and/or gelatin" refers to any of collagen, gelatin, a derivative thereof or a combination of two or more of them. In the present invention, commercially available collagen, gelatin and derivatives thereof may be used as they stand.

The characteristic feature of the method of the invention resides in that a high concentrated mixture with respect to collagen and/or gelatin is first prepared and that the solvent contained in the mixture is gradually eliminated after molding. Accordingly, there is no criteria to the active ingredient contained in the mixture. However, the method of the invention is particularly useful for the preparation of a sustained release formulation associated with a water-soluble drug which has hitherto been difficult to prepare any sustained release formulation. These water-soluble drugs include, for instance, prostaglandins, prostacyclines, various biohormones, tespamin (triethylenethiophosphoramide), interferon, interleukin, tumor necrosis factor and the like. A drug which is slightly soluble in water but exhibits activity even in small dosage, such as adriamycin is another example for use in the present invention. In addition, various antibiotics, chemotherapeutic agents, biologically active substances, anti-aging agents, growth hormones, and anti-inflammatory agents are also employed in the present invention.

In other aspect, the method according to the invention finds use in preparing a sustained release formulation containing a heat-unstable high molecular drug because the method of the invention does not include any step which is carried out under severe conditions such as heat-melting.

The term "high molecular drug" herein used refers to peptides, proteins, glycoproteins, polysaccharides, etc. Particularly suitable high molecular drugs are those which exhibit activity in small dosage and are desired to be continuously administered over a long period of time. Such drugs are exemplified by thrombolytic agents, biological response modifiers, those having a growth promoting activity or those associated with bone metabolism.

Specific examples of the drug having a growth promoting activity are growth hormones (GH), growth hormone releasing factors (GRF) and somatomedins (SM).

GRF is a peptide which has an ability of stimulating growth hormone secretion and they are known as peptides consisting of a number of amino acids of 44, 40, 37 or 29. All of these peptides show the growth hormone releasing activity and any of them and a mixture thereof may be employed in the present invention.

SM means all of the somatomedin group, such as SM-A, SM-B, SM-C and further insulin-like growth factor (IGF)-I, IGF-II as well as MSA (multiplication stimulating activity). It is reported that SM-C is the same as IGF-I. Anyway, all of these peptides or a mixture of two or more thereof may be used in the present invention.

The drug having an activity associated with bone metabolism includes, for example, calcitonin.

The drug having thrombolytic activity includes a tissue plasminogen activator.

Examples of biological response modifiers are interferon (IFN), interleukin (IL), colony-stimulating factor (CSF), macrophage activating factor (MAF), and migration inhibition factor (MIF). The term "interferon" denotes any type of interferons including $\alpha$-, $\beta$-, and $\gamma$-interferons as well as a blend thereof. Likewise, interleukin includes IL-1, IL-2, IL-3, etc., and colony-stimulating factor includes multi-CSF, granulocyte macrophage CSF (GM-CSF), macropharge CSF (M-CSF), granulocyte-CSF (G-CSF) etc., and a mixture thereof.

The method of the present invention is applicable to any of subclass proteins or glycoproteins which is expected to be separated and purified from MAF or MIF during extended studies in the future.

The peptides, proteins and glycoproteins employed in the method of the present invention may be those which have been chemically synthesized or produced by genetic engineering, as well as those of natural source.

The hydrophilic organic solvent employable in the present invention includes alcohols such as methanol and ethanol and ketones such as acetone. A mixture consisting of such hydrophilic organic solvent and water can be employed in the method of the invention. However, the content of the hydrophilic solvent in the mixture should be below 70% by weight.

The sustained release formulation of the invention may be prepared in the manner detailed below.

A uniform and high concentrated mixture with respect to collagen and/or gelatin is first prepared by blending an active ingredient and said collagen and/or gelatin with water or a mixture consisting of water and a hydrophilic organic solvent. For this purpose, for instance, an aqueous solution containing an active ingredient is uniformly admixed with an aqueous solution of collagen and/or gelatin while preventing the generation of foam as small as possible. Thereafter, the mixture is concentrated at low temperature or dried. The drying method is not specified, but it may be dried, for example, by spray-drying, or lyophilization. A small amount of distilled water for injection is added thereto to allow swelling. The swelling time may be about 0.1 to 48 hours. There is no limitation to the temperature under which the swelling step is conducted. However, preferably this step is carried out in a refrigerator. After swelling, an acid, for instance hydrochloric acid, is added thereto until the mixture becomes below pH 5 whereby collagen and/or gelatin is allowed to dissolve, and the whole is thoroughly blended. The time required for blending is about 0.1 to 12 hours. The temperature is arbitrary and a room temperature is preferred.

The above procedure is convenient where the active ingredient is the one which is ordinarily handled in the form of a solution or suspension. However, when the amount of the solution or suspension containing the active ingredient is very small, or when the active ingredient is a solid powder, it may be directly added to an aqueous solution of collagen and/or gelatin which has been prepared by swelling powdery collagen and/or gelatin with addition of a small amount of water and thereafter adding thereto an acid, such as hydrochloric acid. Generally, 0.5 to 0.8 ml of 1N HCl will be required per 1 g of collagen and/or gelatin. A uniform and high concentrated mixture which contains 10 to 40 w/w %, preferably 20 to 30 w/w % of collagen and gelatin is thus obtained.

In the above process, one of the afore-mentioned countermeasures for preventing the fiber-formation should be taken. If possible, the salt concentration of the mixture containing an active ingredient and collagen and/or gelatin is lowered below "fiber-forming concentration". Where the active ingredient is in the form of a solid powder, the lowering of the salt concentration is easily accomplished.

The term "salt" herein used in connection with "the salt concentration" refers to any salt contained as an isotonic agent, buffering agent or stabilizer and includes sodium chloride, sodium dihydrogenphosphate, disodium hydrogenphosphate, sodium citrate, etc.

Where it is impossible to lower the salt concentration, a collagen and/or gelatin solution containing an active ingredient is swollen, acidified, and then added with glucose at the final concentration of 0.1 to 2 mole/l, followed by thoroughly blending in a mortar. Thereafter, the pH of the mixture is adjusted by the addition of aqueous ammonia solution or aqueous sodium hydroxide to neutral, and added, if necessary, with a buffer solution, and blended in a mortar to make a uniform solution. For instance, a mixture of 20 w/v % atelocollagen and 1.0 mole glucose permits addition of 0.75 mole of NaCl without causing fiber-formation. The acidic condition is not essential for blending. However, blending under acidic condition and neutralization of the resultant mixture are advantageous for obtaining a uniform solution. The order of the addition of the above various agents is not critical. The buffer used in this process includes sodium chloride, phosphates and urea, etc.

Instead of taking any of the above procedures, chemically-modified collagen and/or gelatin can be employed in the process of the present invention in place of collagen and/or gelatin. For instance, a 20 w/v % sucinylated atelocollagen solution can be admixed with no less than 2 moles of NaCl without accompanied by fiber-formation.

The next step of the present invention is that the uniform and high concentrated mixture is placed in a cylinder having a given bore, centrifuged to obtain void-free-parts and extruded for molding. The product after molding is then subjected to gradual elimination of the solvent. The bore of the cylinder will vary depending on the size of the desired product. For instance, the use of a bore of 2 mm will give a mini-pellet having a diameter of 1 mm. The centrifugal deaeration may be conducted at a temperature between 20° and 35° C. at 5,000 to 15,000 G for 10 to 60 minutes.

The uniform and high concentrated mixture may also be molded in a template after centrifugal deaeration. Where the molding is conducted using the template, for instance a tube, it is recommendable to refrigerate the mixture which has been charged in the template, and remove the refrigerated product from the template and then subject the product to gradual elimination of the solvent. In the above process, refrigerating time and temperature are not critical. The essential point is that the molded product should have enough hardness to keep its shape when removed from the template.

The gradual elimination of the solvent from the molded product can be achieved by one of the following alternatives.

(A) The product is air-dried by allowing it to stand at room temperature or below for 24 to 72 hours under relative humidity of 50 to 80%. This process is preferably conducted using a desiccator.

(B) The product is immersed in a mixture of water and hydrophilic organic solvent for a given period and this procedure is repeated several times on condition that a mixture containing an increasing amount of the organic solvent is employed each time, thereby the water contained in the product is gradually replaced by the organic solvent. Finally, the organic solvent held by the product may be easily air-dried.

The term "gradual elimination" herein used refers to removal of solvent without losing the shape generated by the molding. Specifically, it means, for example, to control the drying rate below or at 1 mg of water/$mm^2$/24 hours in the above process (A). When the product is dried in the atmosphere beyond this criterion, for instance, under condition that the relative humidity is less than 50%, or when there is non-negligible air flow on the surface of the product, only the surface is first dried and the loss of the shape occurs. It should be noted, however, that the relative humidity higher than 80% makes the drying rate too slow and is not desirable for practical purposes.

The product which has been dried in accordance with the above process may be subjected, if necessary, to additional drying step which, for instance, comprises to place the dried product in a desiccator containing silica gel. Where the drying step is conducted in a laboratory scale, the product may be successfully dried by allowing it to stand at room temperature after placed in a Petri dish with the cap.

In the above process (B), there are employed a set of mixtures consisting of water and a hydrophilic organic solvent, each containing an increasing amount of the organic solvent. Preferred set consists of the mixtures which contain, for example, 50%, 70%, 80%, 90%, 95% and 100% by weight of the organic solvent. As the hydrophilic organic solvent, there may be mentioned alcohols such as methanol and ethanol, ketones such as acetone, which are freely miscible with water. Preferably, the hydrophilic organic solvent used in this step is identical with that used in the process wherein the uniform and high concentrated mixture was prepared.

The gradual elimination of the solvent from the molded product yields a final product which has constant size and weight and in which the active ingredient is uniformly dispersed.

As previously stated, the final product obtained above can be neutralized, if necessary, by contacting the product with ammonia gas or by dipping the same in aqueous ammonia or ethanol containing disodium hydrogenphosphate.

Additional processings can be effected on the final product obtained above for the purpose of further controlling the release rate of the active ingredient. Such processings include the formation of crosslinking, with the crosslinking agent, UV irradiation or γ irradiation among the collagen and/or gelatin contained in the product, or where appropriate, between the collagen and/or gelatin and the active ingredient. The crosslinkage may be of a covalent bond or an ionic bond. The crosslinkage can be effected, for instance, by immersing the product in a suitable crosslinking agent such as an aqueous aldehyde solution (e.g. formaldehyde, acetaldehyde or glutaraldehyde), or an alcohol solution containing a diisocyanate (e.g. hexamethylene diisocyanate), or by contacting the product with a gaseous crosslinking agent selected from the above. These processes for making crosslinking are well known in the art and do not constitute characteristic feature of the present invention. Furthermore, the active ingredient is chemically bound to a polymer backbone-chain of collagen and/or gelatin contained in the product.

The novel method of the present invention is applicable to the preparation of any type of a sustained release formulations having a variety of sizes and shapes, such as spherical, hemispherical, column, tubular, buttony or sheet-like shape as well as needle- or bar-like shape. The formulation produced by the method of the present invention may be administered to a living body, for example, by subcutaneous insertion or implantation into a body cavity, depending on the lesional region to be treated. The formulation may also be pulverized at a low temperature using liquid nitrogen to obtain powder, which may be suspended in a suitable solvent to prepare a sustained release injectable suspension.

The formulation according to the invention may contain pharmaceutically acceptable stabilizers, preservatives or anesthetic agents, as well as various additives for improving the formability into special shapes or controlling the sustained-release ability of the formulation.

FIG. 1 of the accompanying drawing shows the time-course of the blood level of α-interferon when the sustained release formulation containing interferon, which has been prepared in accordance with the above process, is administered to mice.

The following detailed examples are presented by way of illustration of specific embodiments of the invention.

EXAMPLE 1

An aqueous solution (5 ml) containing α-interferon (20 MU/ml) is added to atelocollagen (2 g), and the mixture is allowed to swell for 20 hours in a refrigerator. Distilled water and 1N HCl (1.6 ml) are added thereto to make the final weight of 10 g, and the mixture is thoroughly admixed in a mortar to obtain a uniform liquid mixture. The mixture is charged in a disposable syringe (10 ml) and centrifugally deaerated at 10,000 G for 30 minutes. After attachment of a nozzle having an inner-diameter of 2 mm, the mixture is extruded from the syringe so that the extruded mixture is placed in a linear slot having a semi-circular section on an acrylic sheet. The extruded mixture is dried for 24 hours in a desiccator kept at 65% relative humidity. The dried mixture is neutralized by exposure to ammonia gas, air-dried, and cut. Needle-like shaped pellets having an average diameter of 1 mm ±2% and containing 0.1 MU interferon per piece are thus obtained.

EXAMPLE 2

The deaerated mixture obtained by the same process as described in Example 1 is placed in a spherical split mold having a diameter of 1.7 mm. In the similar manner as described in Example 1, the mixture is dried, removed from the mold, and neutralized by dipping in an aqueous 0.02M $Na_2HPO_4$ 50% ethanol solution. Thereafter, the solid mixture is sequentially dipped in 50, 70, 80, 90, and 95% ethanol, and finally dipped in 100% ethanol until equilibrium is reached. The solid mixture is then air-dried to remove the ethanol. Spherical pellets having an average diameter of 1 mm ±2% and average weight of 0.75 mg ±10% are thus obtained.

EXAMPLE 3

A 30% aqueous solution of gelatin (pH 3.5), which has been obtained by heat-denaturation of atelocollagen, is mixed with a 30% aqueous solution of alelocollagen (pH 3.5) at a ratio of 2:8. The mixture is charged in a syringe, centrifugally deaerated, and introduced into a spherical split mold having a diameter of 1.5 mm. The above processes are conducted at a temperature between 33° and 35° C. After cooling below 30° C., the solid product is removed from the mold, neutralized by dipping in 0.1% aqueous ammonia solution, and thoroughly washed with water. Dehydration is then carried out in the same manner as in Example 2. The resultant product is immersed for 12 hours in ethanol containing 0.1% of hexamethylene diisocyanate in order to obtain the crosslinked product. The product is washed with ethanol and air-dried to provide uniform spherical pellets having a diameter of 1 mm.

EXAMPLE 4

An aqueous solution of growth hormone releasing factor (GRF: 20 mg/ml)(5 ml) and 2 w/v % atelocollagen (pH 3.5)(100 ml) are homogeneously mixed with stirring while preventing generation of foam as small as possible, and the mixture is lyophilized. The solid mixture is then swollen with addition of a small amount of distilled water. The swollen mixture is added with distilled water to make a final weight of 10 g, and thoroughly admixed in a mortar to obtain a uniform mixture. The mixture is treated in the same manner as in Example 1, which gives uniform pellets.

EXAMPLE 5

To an aqueous solution containing 25 w/v % of succinylated atelocollagen is added glucose at a final concentration of 0.5M. Sodium chloride is then added thereto at a final concentration of 1.9M (pH 7.2). The resultant mixture is molded in the same manner as Example 1 to obtain uniform pellets.

EXAMPLE 6

Atelocollagen (20 g) is swollen by the addition of a small amount of distilled water. To the mixture are added 1N HCl (16 ml), glucose (9 g), and saline (1000 ml) containing 0.15M NaCl and 1 MU/ml of α-interferon. The mixture is thoroughly admixed and then concentrated under reduced pressure to 100 ml. After kneading, the mixture is extruded, using a extruder, from a nozzle of 2.0 mm diameter onto the sheet. The extruded product is dried at 20° C., 60% relative humidity, for 24 hours to obtain uniform pellets having 1 mm diameter.

Example 7

A 0.1% human serum albumin solution (1 ml) containing mouse GM-CSF ($1 \times 10^7$ U/ml) and 2 w/v % atelocollagen solution (pH 3.5) (50 ml) are homogeneously mixed with stirring while preventing generation of foam as small as possible, and the mixture is lyophilized. The solid mixture is then swollen with addition of a small amount of distilled water. The swollen mixture is added with distilled water to make a final weight of 5 g, and thoroughly admixed in a mortar to obtain a uniform mixture. The mixture is charged in a disposable syringe (5 ml) and subjected to centrifugal deaeration for 30 minutes at 10,000 G. After attachment of a nozzle having an inner-diameter of 2 mm, the mixture is extruded from the syringe so that the extruded mixture is placed in a linear slot having a semi-circular section on an acrylic sheet. The extruded mixture is dried for 72 hours in a desiccator kept at 75% relative humidity, which is placed in a refrigerator. The dried product is transferred and kept in a silica gel desiccator for 24 hours and cut to mini-pellets. The pellets thus obtained are uniform in size and weight.

EXAMPLE 8

An aqueous solution (5 ml) containing IGF-1 (4 mg/ml) and 2 w/v % atelocollagen solution (pH 3.5)(5 ml) are homogeneously mixed with stirring while preventing generation of foam as small as possible, and the mixture is lyophilized. The solid mixture is then swollen with addition of a small amount of distilled water. The swollen mixture is combined with additional distilled water to make a final weight of 0.5 g and thoroughly admixed in a mortar to obtain a uniform mixture. The mixture is charged in a disposable syringe (1 ml) and treated in the same manner as Example 7 to obtain uniform mini-pellets.

EXAMPLE 9

Powdered atelocollagen (1 g) is mixed with water (2.2 ml) and 1N HCl (0.8 ml) at pH 3.0 to prepare a 25 w/v % atelocollagen solution. The solution is charged in a plastic syringe and centrifugally deaerated at 10,000 G for 30 minutes. Thereafter, the deaerated solution is charged in a Teflon tube (inner-diameter: 1.5 mm, length: 10 cm) and refrigerated at $-40°$ C. for 24 hours. After confirming the complete refrigeration of the solution, the solid substance is extruded using an iron bar. The substance is placed on a plastic Petri dish. The dish, after covered with the cap, is kept at room temperature for 3 days. The dried substance is cut so as to obtain pieces each having 10 mm length. Each of the resultant bar-like shaped pellets is weighed. Table 1 shows the results of this measurement.

TABLE 1

| weight of bar-like product(mg) | weight of bar-like product(mg) | weight of bar-like product(mg) |
|---|---|---|
| 6.70 | 6.38 | 6.63 |
| 6.60 | 6.31 | 6.63 |
| 6.14 | 6.27 | 6.61 |
| 6.87 | 6.38 | 6.44 |
| 6.86 | 6.56 | 6.49 |
| 6.52 | 6.61 | 6.29 |
| 6.36 | 6.59 | 6.62 |
| 6.47 | 6.50 | 6.89 |
| 6.54 | 6.11 | 6.71 |
| 6.36 | 6.47 | 6.47 |
| 6.55 | 6.45 | 6.46 |
| 6.60 | 6.30 | 6.74 |
| 6.11 | 6.39 | 6.52 |
| 6.42 | 6.50 | 6.25 |
| 6.18 | 6.72 | 6.44 |
| 6.27 | 6.37 | 6.48 |
| 6.27 | 6.37 | 6.51 |
| 6.29 | 6.70 | average: |
| 6.25 | 6.37 | 6.47 |
| 6.31 | 6.60 | ± 0.19(mg) |

Standard deviation of 57 samples listed in Table 1 is 0.19, which shows that there is very low dispersion among the samples in connection with their weights.

EXAMPLE 10

Powdered atelocollagen (2 g) is thoroughly admixed with an aqueous solution (5 ml) of α-interferon (20 MU/ml) and $_1$N HCl (1.6 ml), and the mixture is centrifugally deaerated in the similar manner as in Example 1. The deaerated mixture is charged in five Teflon tubes (inner-diameter: 15 mm, length 10 cm). The tubes are refrigerated at $-40°$ C. for 24 hours. The refrigerated products are extruded from the tubes by the use of an iron bar. The products are placed on a Petri dish. After covered with a cap, the dish is kept at room temperature for three days to obtain a bar-like shaped formulation containing α-interferon.

EXAMPLE 11

Sterile and pyrogen-free powdered atelocollagen (2 g) is mixed with growth hormone releasing factor (GRF, 1-29)(120 mg). To the mixture are added an appropriate amount of a 0.02M $Na_2HPO_4$ solution prepared with distilled water and 0.15M NaCl buffer (6 ml) so as to bring the concentration of atelocollagen to 25 w/v %. Subsequently, glucose is added at the final concentration of 0.25M, and the mixture is thoroughly blended. After centrifugal deaeration effected in the similar manner as in Example 1, the mixture is charged in five Teflon tubes (inner-diameter: 1.5 mm, length: 10 cm). The tubes are refrigerated at $-40°$ C. for 24 hours and the resultant solid substance is extruded using an iron bar. The solid substance is placed in the Petri dish, covered with the cap, and kept at room temperature for the purpose of drying. Bar-like formulations containing GRF are thus obtained.

EXPERIMENT 1

The needle-like mini-pellets prepared in Example 1 were subcutaneously administered to three mice and the blood level of α-interferon was measured by radioimmunoassay. As a control, an injectable aqueous solution of α-interferon was subcutaneously administered to another group consisting of three mice and the blood level was measured in the same manner as above. Each mouse received 0.1 MU interferon. The time-course of the blood level is shown in FIG. 1 of the accompanying drawing, wherein vertical and horizontal axes show the blood level of α-interferon (average of three mice, unit/ml) and the timecourse (hours) respectively. The symbols ○ and ● respectively represent the invention and control. FIG. 1 distinctly shows that the pellet of the invention provides a long-term sustained release of α-interferon and that the constant blood level is maintained for up to 72 hours starting from the 3rd hour after administration, which represents an ideal release pattern.

What is claimed is:

1. A method for preparing a sustained release formulation comprising collagen and/or gelatin as a carrier, which comprises:
   (i) blending a physiologically active ingredient together with collagen and/or gelatin, and water or an admixture of water and a hydrophilic organic solvent to produce a uniform and high concentrated mixture containing said collagen and/or gelatin in an amount of 10 to 40 w/v % to produce a uniform and high concentrated mixture;
   (ii) molding the resultant uniform and high concentrated mixture; and
   (iii) gradually eliminating the solvent from the molded product, said blending step being conducted under one of the conditions of:
     (A) maintaining the pH of said mixture below 5 and maintaining the salt concentration of said mixture below the fiber-forming concentration;
     (B) utilizing chemically modified collagen and/or gelatin as the carrier; or
     (C) adding glucose to said mixture during said blending step.

2. A method according to claim 1 wherein the gradual elimination of the solvent consists of air-drying the molded product under atmosphere of the relative humidity of 50 to 80%.

3. A method according to claim 1 wherein the gradual elimination of the solvent consists of immersing the molded product repeatedly in a mixture of water and a hydrophilic organic solvent, on condition that a mixture containing an increasing amount of the organic solvent is employed each time, thereby the water contained in the molded product is gradually replaced by the organic solvent, and finally, removing the organic solvent held by the product by air-drying.

4. A method according to claim 1 wherein the molding process of step (ii) consists of refrigerating the uniform and high concentrated mixture charged in a template and removing the molded product from the template in the refrigerated state.

5. The method according to claim 1, wherein said molding in step (ii) is made by extruding or molding in a template.

6. A method according to claim 1, wherein the amount of collagen and/or gelatin is in the range of 20 to 30 w/v %.

7. A method according to claim 2, wherein said air-drying is conducted at a maximum rate of 1 mg of water/mm$^2$/24 hours.

8. The method according to claim 1, wherein said carrier is collagen.

9. A method for preparing a sustained release formulation comprising collagen and/or gelatin as a carrier, which comprises:
 (i) blending a physiologically active ingredient together with collagen and/or gelatin, and water or an admixture of water and a hydrophilic organic solvent to produce a uniform and high concentrated mixture containing said collagen and/or gelatin in an amount of 10 to 40 w/v % to produce a uniform and high concentrated mixture;
 (ii) molding the resultant uniform and high concentrated mixture; and
 (iii) gradually eliminating the solvent from the molded product to produce a product suitable for subcutaneous insertion or implantation, said blending step being conducted under one of the conditions of:
  (A) maintaining the pH of said mixture below 5 and maintaining the salt concentration of said mixture below the fiber-forming concentration;
  (B) utilizing chemically modified collagen and/or gelatin as the carrier; or
  (C) adding glucose to said mixture during said blending step.

10. A method according to claim 9, wherein the molding process in step (ii) is made by extruding or molding in a template.

11. The method according to claim 9, wherein said carrier is collagen.